United States Patent
Philippe et al.

(10) Patent No.: US 6,359,175 B1
(45) Date of Patent: Mar. 19, 2002

(54) COSMETIC COMPOSITION COMPRISING AN AMIDE AND NOVEL AMIDES

(75) Inventors: Michel Philippe, Wissous; Didier Semeria, Courtry, both of (FR)

(73) Assignee: L'Oreal S.A., Paris (FR)

( * ) Notice: Subject to any disclaimer, the term of this patent is extended or adjusted under 35 U.S.C. 154(b) by 0 days.

(21) Appl. No.: 09/445,588

(22) PCT Filed: May 28, 1999

(86) PCT No.: PCT/FR98/01077

§ 371 Date: Dec. 10, 1999

§ 102(e) Date: Dec. 10, 1999

(87) PCT Pub. No.: WO98/56754

PCT Pub. Date: Dec. 17, 1998

(30) Foreign Application Priority Data

Jun. 11, 1997 (FR) .............................................. 97 07241

(51) Int. Cl.$^7$ .......................... C07C 233/05; A61K 7/42
(52) U.S. Cl. ...................... 564/215; 252/315.1; 424/59; 514/629; 554/35
(58) Field of Search ........................... 564/215; 424/59; 514/629; 252/315.1; 554/35

(56) References Cited

U.S. PATENT DOCUMENTS

| 5,162,315 A | 11/1992 | Rajadhyaksha et al. |
| 5,476,637 A | 12/1995 | Fuhrmann |
| 5,476,643 A | 12/1995 | Fogel |
| 5,516,506 A | 5/1996 | Fogel |

FOREIGN PATENT DOCUMENTS

| DE | 30 09 543 | | 9/1981 |
| EP | 0 518 773 | | 12/1992 |
| GB | 1421744 | * | 1/1976 |
| GB | 2 001 083 | | 1/1979 |
| JP | 62-215537 | | 9/1987 |
| WO | WO 88/04167 | | 6/1988 |
| WO | WO 94/18940 | | 9/1994 |

OTHER PUBLICATIONS

Martine Benoit–Guyod et al., "Recherches dans la série dipropylacétique VIII.—Structures homologues : amides et urées de la propyl–2 pentylamine", Chimica Therapeutica, vol. VII, No. 5, Sep.–Oct. 1972, pp. 393–398.

Chemical Abstracts, vol. 123, No. 2, Jul. 10, 1995 (Abstract No. 19050).

Chemical Abstracts, vol. 125, No. 19, Nov. 4, 1996 (Abstract No. 247066).

English language Derwent Abstract of DE 30 09 543., 1981.

English language abstract of EP 0 518 773., 1992.

English language Derwent Abstract of JP 62–215537, 1987.

* cited by examiner

*Primary Examiner*—Shailendra Kumar
(74) *Attorney, Agent, or Firm*—Finnegan, Henderson, Farabow, Garrett & Dunner, L.L.P.

(57) ABSTRACT

The invention concerns a composition, in particular a cosmetic composition, comprising at least a powder substance and a branched amide used as dispersion agent. The invention also concerns novel branched amides of formula (I').

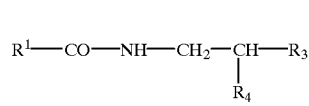

(I')

10 Claims, No Drawings

COSMETIC COMPOSITION COMPRISING AN AMIDE AND NOVEL AMIDES

This application is a 371 of PCT/FR98/01077, filed May 28, 1998.

The present invention relates to a novel composition, in particular a cosmetic composition, comprising specific amides and pulverulent materials. The invention also relates to the use of certain amides as dispersants for pulverulent materials, as well as to a process for dispersing pulverulent materials.

It is known practice to use pulverulent materials such as pigments or fillers in cosmetic compositions for the purpose in particular of giving these compositions a desired color. Certain metal oxide pigments, such as titanium dioxide, are also used for their known appreciable anti-UV properties. However, the incorporation of these pulverulent materials into cosmetic compositions is not always easy to carry out. The reason for this is that the appearance of aggregates is frequently observed and the pigments often tend to sediment out over time; the dispersion of the pigments in the composition is then no longer homogeneous. The sedimentation of the pigments no longer makes it possible to conserve the uniformity of the color of the composition, in particular when it is applied to the skin. This sedimentation can also give rise to a substantial reduction in the efficacy of the antisun protection imparted by pigments with anti-UV properties.

To prevent the aggregation and/or 5 sedimentation of pigments, it has been proposed to use dispersing agents, and in particular branched alkyl esters. For example, patents U.S. Pat. No. 5,476,637 and U.S. Pat. No. 5,516,506 describe the use of neopentyl glycol esters to help disperse pigments. According to patent application WO 94/18940, it is also known practice to improve the dispersion of titanium oxide pigments by using branched organic compounds such as esters, ethers, hydrocarbons or silicones, and in particular octyldodecyl neopentanoate.

Although these dispersants described in the prior art make it possible to disperse the pigments commonly used in cosmetics, the stability over time of these dispersions is, however, unsatisfactory. The reason for this is that, after storage for several hours, or even several days, it is found that the pigment dispersion does not retain its homogeneity since the pigments sediment out over time.

Moreover, it is known practice from patent U.S. Pat. No. 5,162,315 and patent application JP-A-62-215,537, to use amides comprising at least two alkyl chains to improve the penetration of pharmaceutical active agents into the skin. In patent application WO 88/04167, amides comprising two alkyl chains are used in an antisun or moisturizing composition, in the form of an emulsion, to impart moisture resistance to the composition.

An object of the present invention is to allow the preparation and production of a composition which comprises homogeneously dispersed pulverulent materials and which is stable over time.

The Applicant has discovered, surprisingly and unexpectedly, that by using certain branched amides, an entirely stable dispersion of pulverulent materials can be obtained. Furthermore, the stability of the dispersion thus obtained can be preserved for more than one week, or even more than one month.

Thus, the invention relates to a composition comprising at least one pulverulent material and at least one amide of formula (I) below:

$$R^1-CO-NH-R^2 \qquad (I)$$

in which $R^1$ and $R^2$, independently of each other, denote a saturated or unsaturated, branched alkyl radical comprising from 3 to 30 carbon atoms. Preferably, $R^1$ and $R^2$, independently of each other, denote a saturated branched alkyl radical containing from 3 to 20 carbon atoms. More preferably, $R^1$ comprises from 3 to 10 carbon atoms and $R^2$ comprises from 10 to 20 carbon atoms.

Advantageously, $R^2$ denotes a branched radical of formula (II):

in which $R_3$ and $R_4$, independently of each other, denote a linear alkyl radical containing from 1 to 27 carbon atoms, with the proviso that the total number of carbon atoms in the radical of formula (II) is less than or equal to 30. Preferably, $R_3$ and $R_4$, independently of each other, contain from 2 to 12 carbon atoms, and more preferably from 2 to 10 carbon atoms.

Groups $R^1$ which may be mentioned, for example, are tert-butyl and 2,4,4-trimethylpentyl groups.

Groups $R^2$ which may be mentioned are, in particular, 2-octyldodecyl and 2-butyloctyl groups.

Among the preferred compounds corresponding to the general formula (I), mention may be made in particular of:

N-neopentanoyl-2-octyldodecylamine,
N-neopentanoyl-2-butyloctylamine,
N-(3,5,5-trimethylhexanoyl) 2-octyldodecylamine,
N-(3,5,5-trimethylhexanoyl) 2-butyloctylamine.

The compounds of formula (I) are preferably present in a content ranging from 0.1% to 50% by weight relative to the total weight of the composition, and better still from 2 to 20%.

The pulverulent materials present in the composition can be chosen from pigments, nacres and/or fillers. They are preferably present in a proportion of from 0.1 to 80% by weight relative to the total weight of the composition.

Among the pigments which may be mentioned are inorganic pigments such as titanium oxide, zinc oxide, iron oxide, zirconium oxide and cerium oxide, or mixtures thereof. Nanopigments of these metal oxides which are known for their anti-UV properties can also be used. These nanopigments are used in a known manner in antisun compositions. The term "nanopigments" means pigments whose average primary particle size does not exceed 100 nm, this size preferably being between 5 nm and 100 nm and even more preferably between 10 and 50 nm. Such coated or uncoated metal oxide nanopigments are products known to those skilled in the art and are described in particular in patent application EP-A-0,518,773, the teaching of which is, in this respect, included in the present description by way of reference.

Inorganic pigments which may also be mentioned are chromium oxide, manganese violet, ultramarine blue, chromium hydrate and ferric blue. The organic pigments can be chosen from carbon black, pigments of D&C type, and lakes based on cochineal carmine.

The nacres can be chosen from white nacreous pigments such as mica coated with titanium oxide or with bismuth oxychloride, coloured nacreous pigments such as titanium mica coated with iron oxides, titanium mica with, in particular, ferric blue or chromium oxide, titanium mica with an organic pigment of the abovementioned type, as well as nacreous pigments based on bismuth oxychloride.

The fillers can be inorganic or organic, and lamellar or spherical. Mention may be made of talc, mica, silica, kaolin, Nylon powder, poly-β-alanine powder and polyethylene powder, Teflon, lauroyllysine, starch, titanium mica, natural mother-of-pearl, boron nitride, tetrafluoroethylene polymer powders, hollow microspheres such as Expancel (Nobel Industrie), Polytrap (Dow Corning) and silicone resin microbeads (Tospearls from Toshiba, for example), zinc oxide, titanium oxide, precipitated calcium carbonate, magnesium carbonate and hydrocarbonate, hydroxyapatite, hollow silica microspheres (Silica Beads from Maprecos), glass or ceramic microcapsules; metal soaps derived from organic carboxylic acids containing from 8 to 22 carbon atoms, preferably from 12 to 18 carbon atoms, for example zinc, magnesium or lithium stearate, zinc laurate or magnesium myristate.

A subject of the invention is also the amides of formula (I') below:

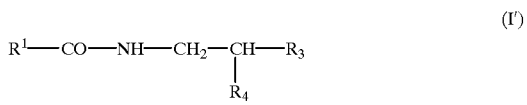

in which
R$^1$ denotes a saturated or unsaturated, branched alkyl radical containing from 3 to 30 carbon atoms,
R$_3$ and R$_4$, independently of each other, denote a linear alkyl radical containing from 1 to 27 carbon atoms, with the proviso that the total number of carbon atoms in the radical —CH$_2$—CH(R$_3$) (R$_4$) of formula (I') is less than or equal to 30.

Preferably, R$^1$, R$_3$ and R$_4$ have the preferred meanings mentioned above for the compounds of formula (I).

These compounds are generally in the form of an oily liquid. It has thus been observed that the dispersion of pulverulent materials in the amides according to the invention is better, more homogeneous and more stable over time than the dispersion of these same pulverulent materials in the oils of the prior art.

The mixture of pulverulent materials and of branched amides which is prepared beforehand can be introduced, for example, into a support which is acceptable for the intended use, in particular into a cosmetically acceptable support.

The said branched amides and the pulverulent materials can also be introduced separately, either into a pre-prepared composition, in particular a cosmetic composition, or directly during the mixing of all of the constituents of the composition, in particular a cosmetic composition, according to processes that are well known to those skilled in the art.

The composition according to the invention can also comprise at least one oil, chosen in particular from plant, animal, mineral or synthetic oils. Needless to say, a person skilled in the art will take care to use oils which are not harmful to correct dispersing of the pulverulent materials in the composition, in acceptable amounts so as not to adversely affect the said dispersion.

According to a specific embodiment of the composition of the invention, the composition comprises as sole oil a compound of formula (I) as defined above.

The composition can also comprise other fatty substances, such as waxes, which can be chosen from the animal, fossil, plant, mineral or synthetic waxes known per se.

Advantageously, the composition according to the invention can comprise a cosmetically acceptable support.

The composition of the invention can also contain at least one additive chosen from thickeners, surfactants, fragrances, preserving agents, sunscreens, proteins, vitamins, polymers and any other additive conventionally used in cosmetics. The precise amount of each additive is readily determined by a person skilled in the art on the basis of its nature and its function.

Needless to say, a person skilled in the art will take care to select this or these optional additives and/or the amounts thereof such that the advantageous properties, and in particular that of dispersing of the pulverulezit materials, intrinsically associated with the compounds of formula (I) in accordance with the invention are not, or are not substantially, adversely affected by the addition or additions envisaged.

The processes for manufacturing the compositions of the invention do not differ in any way from the processes conventionally used, in particular in cosmetics, and which are entirely known to those skilled in the art.

The composition according to the invention can be in the form of a dispersion, an emulsion, in particular a water-in-oil or oil-in-water emulsion, or alternatively in the form of a soft paste.

The cosmetic compositions according to the invention can be in the form of a make-up composition, a skincare composition, a hair composition or an antisun composition.

The make-up compositions can be in the form of an eyeshadow, a face powder, an eyeliner, a foundation, a blusher, a mascara, a lipstick, a lipcare stick, a concealer composition or a tinted cream.

The hair compositions can be in the form of a shampoo, a lotion, a gel, an emulsion, a nonionic vesicular dispersion or a lacquer for the hair and can is constitute, for example, a rinse-out composition, to be applied before or after shampooing, before or after dyeing or bleaching, or before, during or after permanent-waving or straightening the hair, a styling or treating lotion or gel, a blow-drying or hair-setting lotion or gel, or a composition for permanent-waving, straightening, dyeing or bleaching the hair.

The invention also relates to the use of an amide of formula (I) as defined above as an agent for dispersing pulverulent materials. The expression "dispersing agent" means a compound capable of helping to disperse the said pulverulent materials.

A subject of the invention is also a process for dispersing pulverulent materials, characterized in that the said pulverulent materials are dispersed in a composition comprising at least one amide of formula (I) as defined above.

Examples illustrating the present invention will now be given without, however, limiting it.

EXAMPLE 1

Preparation of N-neopentanoyl-2-butyloctylamine 10.4 g of pivalic acid and 17.2 g of 2-butyloctylamine were mixed together in the tube of a microwave machine (Maxidigest™ MX 350 from the company Prolabo; frequency 2450±50 MHz, modulable power 300 W). After irradiation for about 1 hour at 160° C.±10° C., the reaction mixture was dissolved in heptane and then purified on silica. 19 g of the desired amide were obtained.

The $^1$H NMR spectrum is in agreement with the expected structure.
Elemental analysis: $C_{13}H_{37}NO$

|            | C %   | H %   | N %  | O %  |
|------------|-------|-------|------|------|
| Calculated | 75.84 | 13.01 | 5.20 | 5.95 |
| Found      | 75.88 | 12.93 | 5.12 | 6.18 |

EXAMPLE 2

Preparation of N-neopentanoyl-2-octyl dodecyl amine 62 ml of pivaloyl chloride were dissolved in 180 ml of heptane and then added to 150 g of 2-octyldodecylamine at a temperature of 60° C. After addition of 70 ml of triethylamine, the reaction medium was stirred for 2 hours and then purified on silica. 118 g of the desired amide were thus obtained.

The $^1$H NMR spectrum is in agreement with the expected structure.
Elemental Analysis: $C_{26}H_{42}NO$

|            | C %   | H %   | N %  | O %  |
|------------|-------|-------|------|------|
| Calculated | 78.67 | 13.47 | 3.67 | 4.19 |
| Found      | 78.54 | 13.40 | 3.63 | 4.25 |

EXAMPLE 3

Preparation of N-(3,5,5-trimethylhexanoyl)- 2-octyldodecylamine 3.6 g of 3,5,5-trimethylhexanoic acid and 6.8 g. of 2-octyldodecylamine were mixed together in the tube of a microwave machine (Maxidigest™ MX 350 from the company Prolabo; frequency 2450±50 MHz, modulable power 300 W). After irradiation for about 50 minutes at 170° C.±10° C., the reaction mixture was dissolved in heptane and then purified on silica. 7 g of the desired amide were obtained.

The $^1$H NMR spectrum is in agreement with the expected structure. Elemental analysis: $C_{29}H_{59}NO$

|            | C %   | H %   | N %  | O %  |
|------------|-------|-------|------|------|
| Calculated | 79.63 | 13.50 | 3.20 | 3.66 |
| Found      | 79.75 | 13.32 | 3.16 | 3.93 |

EXAMPLE 4

Preparation of N-(3,5,5-trimethylhexanoyl)-2-butyloctylamine 29.2 g of 3,5,5-trimethylhexanoic acid and 34.2 g of 2-butyloctylamine were mixed together in an open Pyrex container and placed in a microwave oven (Menumaster™3100 i; frequency 2450, power at a setting of 30%: 1400 W). After 6 irradiations of about 5 minutes (for each irradiation), the reaction mixture was dissolved in heptane and then purified on silica. 46 g (77%) of the desired amide were obtained.

The $^1$H NMR spectrum is in agreement with the expected structure.
Elemental Analysis: $C_{21}lH_{42}NO$

|            | C %   | H %   | N %  | O %  |
|------------|-------|-------|------|------|
| Calculated | 77.54 | 13.23 | 4.31 | 4.92 |
| Found      | 77.45 | 13.06 | 4.23 | 5.12 |

EXAMPLE 5

Comparative Examples Regarding the Dispersion Properties

The sedimentation speed of a pigment dispersed in various oils was measured.
Protocol:

A mixture of pigment and oil comprising 5% pigment was prepared. This mixture was stirred for 20 hours at 30° C. 10 ml of the dispersion obtained after the stirring were then placed in a graduated tube. Next, the volume of pigment deposited at the bottom of the tube (pellet) as a function of time was measured. The volume of the supernatant remaining in the tube was thus deduced.

The pigment used is the red iron oxide sold under the name "Sicomet Brun ZP 3569" from the company BASF.
Results:

The volume of supernatant (in ml), for each oil tested, measured over time up to about 200 hours, is given.

The following results were obtained:

a) oils according to the invention:

| Hours     | 0  | 1  | 9  | 24 | 49 | 72 | 147 | 201 |
|-----------|----|----|----|----|----|----|-----|-----|
| Oil No. 1 | 7  | 7  | 7  | 7  | 7  | 7  | 7   | 7   |
| Oil No. 2 | 10 | 10 | 10 | 10 | 10 | 10 | 10  | 10  |
| Oil No. 3 | 10 | 10 | 10 | 10 | 10 | 10 | 10  | 10  |
| Oil No. 4 | 10 | 10 | 10 | 10 | 10 | 10 | 10  | 10  |

Oil No. 1: Compound of Example 1
Oil No. 2: Compound of Example 2
Oil No. 3: Compound of Example 3
Oil No. 4: Compound of Example 4

It was found that the volume of the supernatant is constant with the 4 branched oils according to the invention. These oils thus make it possible to obtain a stable dispersion of the pigment.

b) oils not forming part of the invention:

| Hours | 0   | 6   | 12  | 25   | 50  | 100 | 150 | 200 |
|-------|-----|-----|-----|------|-----|-----|-----|-----|
| Oil A | 9   | 7   | 7   | 6.5  | 6.5 | 6.5 | 6.5 | 6.5 |
| Oil B | 10  | 9.9 | 9.8 | 9.5  | 9   | 7.5 | 4   | 3.8 |
| Oil C | 8   | 5.2 | 4.8 | 4.8  | 4.8 | 4.8 | 4.8 | 4.8 |
| Oil D | 6.5 | 4   | 3.9 | 3.8  | 3.8 | 3.8 | 3.8 | 3.8 |
| Oil E | —   | 9   | 6.5 | 2.75 | 2.4 | 2   | 1.9 | 1.8 |

Oil A: Parleam oil
Oil B: Castor oil
Oil C: Silicone oil (Silicone Oil L-45 10 cst from Union Carbide)
Oil D: Octyldoceyl neopentanoate
Oil E: Phenylated silicone oil (Dow Corning 556 Cosmetic Fluid from Dow Corning)

It was found that with the 5 oils not forming part of the invention, the volume of supernatant decreases after 6 hours, the decrease being even large after 200 hours. The dispersions of pigments in these oils are thus not stable over time, unlike the dispersions in oils according to the invention.

EXAMPLE 6

An oil-in-water emulsion having the composition below was prepared:

| | | |
|---|---|---|
| Mixture of cetylstearyl alcohol and of cetylstearyl alcohol oxyethylenated with 33 mol of ethylene oxide (80/20) ("Dehsconet 390" from the company Tensia) | | 7 g |
| Mixture of glyceryl mono- and distearate ("Cerasynth SD" from the company ISP) | | 2 g |
| Cetyl alcohol | | 1.5 g |
| Polydimethylsiloxane ("DC200 Fluid" from Dow Corning) | | 1.5 g |
| Compound of Example 2 | | 10 g |
| Titanium oxide nanopigment (MT 100 T from the company Tayca) | | 5 g |
| Glycerol | | 20 g |
| Preserving agents | qs | |
| Demineralized water | qs | 100 g |

A fluid cream in which the titanium oxide nanopigments are homogeneously dispersed in the composition was obtained. This cream is used as an antisun composition for the face.

What is claimed is:

1. A compound chosen from N-neopentanoyl-2-octyldodecylamine, N-neopentanoyl-2-butyloctylamine, N-(3,5,5-trimethylhexanoyl)-2-octyidodecylamine, and N-(3,5,5-trimethylhexanoyl)-2-butyloctylamine.

2. A composition comprising at least one pulverulent material and at least one amide chosen from N-neopentanoyl-2-octyidodecylamine, N-neopentanoyl-2-butyloctylamine, N-(3,5,5-trimethylhexanoyl)-2-octyidodecylamine, and N-(3,5,5-trimethylhexanoyl)-2-butyloctylamine.

3. A composition according to claim 2, wherein said at least one pulverulent material is chosen from pigments, fillers and nacres.

4. A composition according to claim 2, wherein said at least one amide is present in an amount ranging from 0.1% to 50% by weight, relative to the total weight of the composition.

5. A composition according to claim 4, wherein said at least one amide is present in an amount ranging from 2 to 20% by weight, relative to the total weight of the composition.

6. A composition according to claim 2, wherein said at least one pulverulent material is present in an amount ranging from 0.1% to 80% by weight, relative to the total weight of the composition.

7. A composition according to claim 2, wherein said composition comprises a cosmetically acceptable support.

8. A cosmetic composition according to claim 7, wherein said composition is in the form of a dispersion, an emulsion or a soft paste.

9. A cosmetic composition according to claim 7, wherein said composition is in the form of a make-up composition, a skincare composition, a hair composition or an antisun composition.

10. A process for dispersing at least one pulverulent material, said process comprising dispersing said at least one pulverulent material in a composition comprising at least one amide chosen from N-neopentanoyl-2-octyldodecylamine, N-neopentanoyl-2-butyloctylamine, N-(3,5,5-trimethylhexanoyl)-2-octyldodecylamine, and N-(3,5,5-trimethylhexanoyl)-2-butyloctylamine.

* * * * *

UNITED STATES PATENT AND TRADEMARK OFFICE
CERTIFICATE OF CORRECTION

PATENT NO.    : 6,359,175 B1
DATED         : March 19, 2002
INVENTOR(S)   : Michel Philippe et al.

It is certified that error appears in the above-identified patent and that said Letters Patent is hereby corrected as shown below:

<u>Column 7,</u>
Line 30, "octyidodecylamine" should read -- octyldodecylamine --.
Line 34, "octyidodecylamine" should read -- octyldodecylamine --.

<u>Column 8,</u>
Line 1, "octyidodecylamine" should read -- octyldodecylamine --.

Signed and Sealed this

Twenty-eighth Day of May, 2002

Attest:

JAMES E. ROGAN
Attesting Officer      Director of the United States Patent and Trademark Office